US010233418B2

(12) United States Patent
Schmid et al.

(10) Patent No.: US 10,233,418 B2
(45) Date of Patent: Mar. 19, 2019

(54) DEVICE AND METHOD FOR WETTING A SAMPLE WITH AN AEROSOL

(71) Applicant: Helmholtz Zentrum Muenchen Deutsches Forschungszentrum fuer Gesundheit und Umwelt GmbH, Neuherberg (DE)

(72) Inventors: Otmar Schmid, Munich (DE); Anke-G Lenz, Munich (DE); Bernd Lentner, Erding (DE); Oliver Eickelberg, Munich (DE)

(73) Assignee: Helmholtz Zentrum Muenchen Deutsche Forschungszentrum fuer Gesundheit und Umwelt GmbH, Neuherberg (DE)

( * ) Notice: Subject to any disclaimer, the term of this patent is extended or adjusted under 35 U.S.C. 154(b) by 186 days.

(21) Appl. No.: 14/861,336

(22) Filed: Sep. 22, 2015

(65) Prior Publication Data

US 2016/0010047 A1    Jan. 14, 2016

Related U.S. Application Data

(63) Continuation of application No. PCT/EP2014/055722, filed on Mar. 21, 2014.

(30) Foreign Application Priority Data

Mar. 22, 2013   (DE) .................. 10 2013 005 010

(51) Int. Cl.
*C12M 1/00* (2006.01)
*C12M 1/12* (2006.01)
(Continued)

(52) U.S. Cl.
CPC ......... *C12M 29/06* (2013.01); *B05B 13/0292* (2013.01); *B05B 16/00* (2018.02);
(Continued)

(58) Field of Classification Search
CPC ...... C12M 29/06; C12M 25/06; C12M 41/46; B05B 13/0292; B05B 15/12; G01N 33/5044; G01N 33/5014
See application file for complete search history.

(56) References Cited

U.S. PATENT DOCUMENTS

| 4,857,464 A | 8/1989 | Weathers et al. |
| 2009/0023194 A1 | 1/2009 | Schmidt et al. |
| 2015/0079670 A1* | 3/2015 | Domansky ........... A61M 11/005 435/305.1 |

FOREIGN PATENT DOCUMENTS

| DE | 37 79 442 T2 | 1/1993 |
| DE | 10 2005 061 371 A1 | 6/2007 |

(Continued)

OTHER PUBLICATIONS

Paur et al., "In-vitro cell exposure studies for the assessment of nanoparticle toxicity in the lung—A dialogue between aerosol science and biology," J. of Aerosol Sci., vol. 42, pp. 668-692 (2011).
(Continued)

*Primary Examiner* — Michael L Hobbs
(74) *Attorney, Agent, or Firm* — Muncy, Geissler, Olds & Lowe, P.C.

(57) ABSTRACT

A device for wetting at least one sample by means of an aerosol, the device has: side walls, a base region which is bounded by the side walls, the base region adapted for receiving or interacting with a positioning device for positioning the sample, a cover region, which sits vertically opposite the base region and is bounded by the side walls. The device forms an exposure chamber and an aerosolizing device for producing an aerosol, which is arranged in the vicinity of the cover region. The aerosolizing device is arranged above the base region in such a way that the aerosolizing device at least partially covers the base region in a vertical plan view. A method for wetting at least one (Continued)

sample by an aerosol is also provided that includes the steps of: providing at least one sample, producing a cloud above the at least one sample in a position which at least partially covers the base region in a vertical plan view, and allowing the cloud to descend in the direction of the sample.

23 Claims, 2 Drawing Sheets

(51) Int. Cl.
    *C12M 1/34*     (2006.01)
    *B05B 13/02*     (2006.01)
    *G01N 33/50*     (2006.01)
    *B05B 16/00*     (2018.01)

(52) U.S. Cl.
    CPC ............ *C12M 25/06* (2013.01); *C12M 41/46* (2013.01); *G01N 33/5014* (2013.01); *G01N 33/5044* (2013.01)

(56) References Cited

FOREIGN PATENT DOCUMENTS

| | | |
|---|---|---|
| DE | 10 2009 016 364 A1 | 10/2010 |
| JP | H 08-112560 A | 5/1996 |

OTHER PUBLICATIONS

Lenz et al., "A dose-controlled system for air-liquid interface cell exposure and application to zinc oxide nanoparticles," Particle and Fibre Toxicology, vol. 6, No. 32, pp. 1-17 (2009).

Blank et al., "An Optimized In vitro Model of the Respiratory Tract Wall to Study Particle Cell Interactions," J. of Aerosol Medicine, vol. 19, No. 3, pp. 392-405 (2006).

Brandenberger et al., "Effects and uptake of gold nanoparticles deposited at the air-liquid interface of a human epithelial airway model," Toxicology & Applied Pharm., vol. 242, No. 1, pp. 56-65 (Jan. 1, 2010).

\* cited by examiner

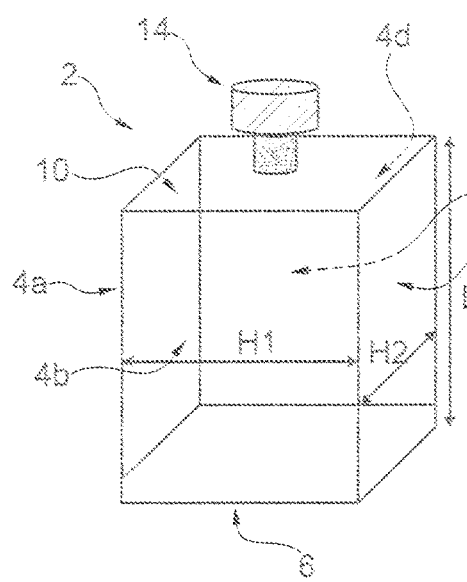
Fig. 1
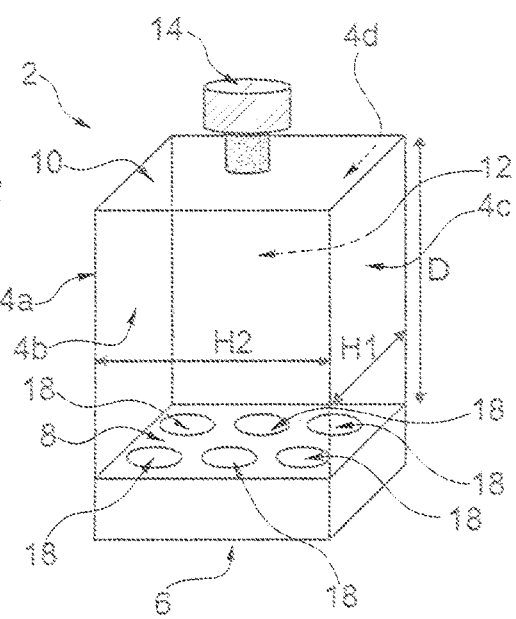
Fig. 2
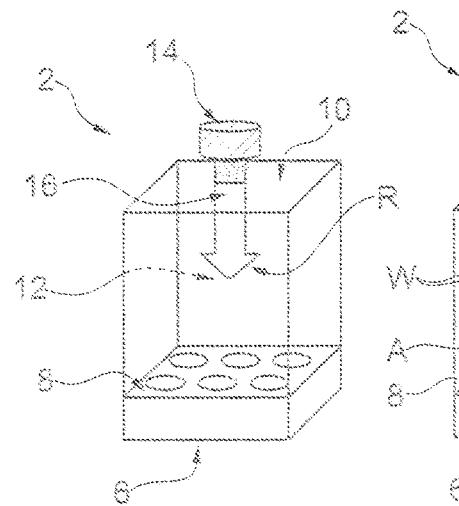
Fig. 3a
Fig. 3b
Fig. 3c

DEVICE AND METHOD FOR WETTING A SAMPLE WITH AN AEROSOL

This nonprovisional application is a continuation of International Application No. PCT/EP2014/055722, which was filed on Mar. 21, 2014, and which claims priority to German Patent Application No. 10 2013 005 010.3, which was filed in Germany on Mar. 22, 2013, and which are both herein incorporated by reference.

BACKGROUND OF THE INVENTION

Field of the Invention

The present invention relates to a device for wetting a sample with an aerosol, preferably a biological sample, for example, a cell sample, in particular at the air-liquid interface. The invention further relates to a corresponding method for wetting a sample with an aerosol. The sample is particularly made up of cells, preferably epithelial cells, most preferably lung cells.

Description of the Background Art

In experiments, it is often necessary to expose a sample, such as cells, to a substance, in particular to a pharmaceutically active substance, e.g. for drug screening, or to a toxic substance, e.g. for toxicity studies.

Usually, in vitro cell experiments are performed for this purpose. Here, an active agent or a toxicologically active substance is added to a sample of cells under so-called submerged cell culture conditions. In such submerged cell culture conditions, the cells are fully covered by the cell medium and the test substance, such as a pharmaceutically active substance or a toxic substance, is pipetted directly into the cell medium.

For epithelial cells, i.e. cells that bound the body to the outside, such as lung epithelial cells, skin cells or retinal cells, this situation is, however, unrealistic because the epithelial cells typically form an air-liquid interface (ALI) in the body. This means that on one side of the epithelial cells there is air or general-purpose gas, and on the other side interstitial tissue or general-purpose liquid.

For studies and experiments on such cells, the complete immersion of such cells in the cell medium is physiologically unrealistic. At the same time, studies or experiments on such cells are often of interest. This is especially true for efficacy and toxicity studies with substances administered by inhalation, for example for inhalation therapies or studies on occupational safety in regards to handling aerosolizable materials, in particular nanomaterials.

Studies at the ALI are used, for example, to analyze the effects of aerosol borne substances (e.g. active agents, toxins, nanoparticles) on cells. What is paramount here is in particular the effect on cells located at the air/bodily fluids contact surface, for example, on epithelial cells of the lung, skin or retina. In inhalation therapy, aerosolized agents are selectively applied to the lung epithelium to treat lung diseases or systemic diseases. In addition, the lung also offers the most important gateway for dealing with many toxic or potentially toxic substances such as environmental dust or nanomaterials in the workplace.

In order to examine those epithelial cells under preferably physiological conditions, several methods have been developed that simulate such an ALI environment. In particular, by means of Transwell inserts, cells at the ALI can also be cultured in standard microtiter plates. Culturing epithelial cells at the ALI is generally physiologically more realistic and therefore, with respect to the effect of substances, potentially more meaningful than the submerged cell cultures described above.

There is therefore a basic need to provide a suitable system for studies and experiments on such ALI cell cultures with which a substance can be evenly applied to ALI cell cultures in a thin layer (e.g. approximately 10-100 microns). Such substances typically include liquid aerosolized agents, but may also include dry substances. Especially for pharmaceutical studies with some very expensive substances, a high deposition efficiency and a uniform distribution of the aerosolized substance on the ALI cells is beneficial. Since neither a suitable device nor a corresponding method have yet been established, the use of ALI cell cultures in pharmaceutical studies and experiments is still relatively limited.

A few systems already exist which aim to coat (lung) cells at the ALI with aerosolized substances. Based on the approach used for the following technological challenges, these substances can be divided into different categories. On the one hand, there is the challenge of transporting the aerosolized substance to the cells (transport) and on the other hand, the object of depositing the aerosol on the cells (deposition).

According to the system in DE102009016364A1, the aerosol is transported to the cells by an air flow (transport: air flow) and deposited by diffusion and/or sedimentation (depending on the size and mass of the aerosol) on the cells.

It is further known to use air flow to transport an aerosol, wherein the deposition occurs electrostatically. Here, the aerosols are initially charged electrostatically and then deposited on the cells electrophoretically in an electric field.

It is also known to apply the cells from a relatively small distance by direct "spraying". Here, transport takes place by generating high-speed aerosols (for example by means of a high pressure nozzle or a quick carrier air stream) and by depositing on the cells via inertial impaction. These types of systems often have the disadvantage of not being able to guarantee the uniform distribution of the aerosols on the cells, or that the operation of these systems is technically very complex.

Often, the known systems can only be used for toxicologically relevant dry aerosols, but not for pharmaceutical liquid aerosols. In addition, the usable particle sizes are often limited, e.g. to below 1 micron. Larger aerosols, for example, greater than 1 micron, such as those used for inhalation therapy, are often not possible.

Many of the known systems also have a very low substance deposition rate, of, for example, about 0.1 $\mu m/cm^2/h$ or approximately 0.1 $nL/cm^2/h$ for aqueous solutions (Paur et al. Journal of Aerosol Science 42 (2011) 668-692, and in here, Table 3), and therefore require very long exposure times of several hours to several days in order to elicit measurable cell-biological responses. Appropriate processes and equipment are very expensive and time-consuming and also make it difficult to work with cells that can be cultured only for 7 days. Operation and quality control also prove to be complex. The (cell) deposition efficiency (percentage of material invested in the aerosol generator which is deposited on the cells) of the known systems is usually far less than 100%, for example, less than 1%, which is sometimes caused by a low deposition efficiency of the aerosols on the cells and by substance losses (residues) in the aerosol generator and in the supply lines. Electrostatic deposition systems also prove to be disadvantageous since the cargo volumes that cannot be avoided could have a distorting effect on the cell response. In addition, some of the known systems are disadvantageous in that they do not allow even or uniform distribution of the substance on the cells. Thus, in particular, no comparable and reproducible dosimetry on the cells is possible. Due to the uncontrolled conditions, a reliable dose-response relationship is difficult to determine. Finally, solutions that deposit the material by inertial impaction are disadvantageous since the cells, among other things, suffer under the high inflow velocity of the aerosol.

Most of the known systems have in common that the aerosol is carried to an exposure chamber via a continuous airflow, requiring a corresponding technological outlay. An example of such a system is the Air-Liquid Interface Cell Exposure system, short ALICE (described in Lenz, A G, E. Karg, B. Lentner, V. Dittrich, C. Brandenberger, B. Rothen-Rutishauser, H. Schulz, G. A. Ferron and O. Schmid, A dose-controlled system for air-liquid interface cell exposure and application to zinc oxide nanoparticles, Particle and Fibre Toxicology 6 (32), 1-17, 2009). An aerosol cloud is transported from one side to an exposure chamber by means of an external air flow. There, the aerosol cloud descends, forms a vortex and then forms a mist that sediments onto the cells, thereby wetting the cells with the substance. The aerosol-depleted air is then removed on the other side of the exposure chamber. This system has a relatively small cell deposition efficiency of approximately 7% and takes up a lot of space (about 1 $m^3$). It can therefore not be operated under a laminar flow cabinet. Furthermore, it has a very complicated technical structure and is therefore more costly to operate. Among other things, the system requires a humidifier, a pump and an air flow meter for generating an external air flow, as well as a droplet trap to avoid disturbances in the exposure process. In addition, the nebulizer is arranged laterally adjacent to the exposure chamber and the system is operated with an external air flow, i.e. in particular, is not operated airflow-free.

Another method which is operated airflow-free was introduced by F. Blank in Blank F, Rothen-Rutishauser B M, Schurch S, Gehr P: An optimized in vitro model of the respiratory tract wall to study particle cell interactions. Journal of Aerosol Medicine-Deposition Clearance and Effects in the Lung, 19(3):392-405, 2006. In this method, a sample is wetted by direct spraying, wherein the sprayer is positioned 12 cm above the sample. The system generates an aerosol spray and deposits the aerosol on the sample via inertial impaction. No sedimentation or cloud effects are used or harnessed. In addition, the system is open (without side walls or cover region) and the method provided herein only achieves a not specified but probably relatively low deposition efficiency. Furthermore, such a spray features a droplet distribution that is heterogeneous at only a very short distance from the production site. Therefore, such a method is not suitable for providing a homogeneous distribution of substances onto samples that are spaced over an area of 100 $cm^2$ or more. Moreover, the reproducibility of the wetting of the sample is not guaranteed because the nebulizer used (MicroSprayer, Penn-Century Inc., USA) is operated manually.

SUMMARY OF THE INVENTION

It is therefore a first object of the present invention to provide an alternative and preferably improved device and an improved method. The purpose of this device or this method is to mitigate or resolve the above-mentioned problems.

In other words, it is therefore an object of the present invention to provide a device and a method for the rapid, simple, uniform and/or reproducible application of a substance or an aerosol (in particular of a liquid or solid substance) to a sample, in particular to an ALI cell culture. Furthermore, this device or this method should be suitable for applying the aerosol with a high deposition rate (aerosol mass per time per cell-covered area).

It is also an object of the present invention to design such device or method as efficient, user-friendly and dosimetrically exact. Preferably, the method itself should not result in biological effects on the cells or tissue sections.

In particular, the present invention relates to a novel system (device, method and use) for the aerosol exposure of a sample. This sample may be a biological sample, for example, cells. These cells can be available in the form of individual cells, of a cell complex (up to organs), tissue sections and/or cultured cells, for example, as a layer of cultured cells. In particular, these may be cells at the air-liquid interface (ALI). Furthermore, it may also be that this sample is made up of material samples, such as metal, plastic and/or glass.

According to an exemplary embodiment, the invention comprises a device for wetting at least one sample by means of an aerosol. An aerosol is hereby understood to be a mixture of a substance with a gas, for example, air. The substance may exist in liquid or solid form, for example, as droplets or dust. In other words, the aerosol is a mixture of solid and/or liquid airborne particles and a gas. The device comprises side walls that are, preferably, essentially vertical, and a base region. During normal use, the base region is arranged at the base of the device, particularly with respect to the gravitational direction. It is preferably bounded by side walls, particularly laterally. The base region is preferably suited for receiving, or for interacting with, a positioning device for positioning the sample, or features such a positioning device. The device further comprises a cover region which is vertically opposed (at the top) to the base region, and which is preferably bounded, particularly laterally, by the side walls. The cover region is preferably suited for receiving, or for interacting with, a top or a cover, or features such. The device forms an aerosol exposure chamber. The term exposure chamber is in particular understood to mean the space defined by the device which is separated from its surroundings by the side walls, the base region and the cover region. The chamber also includes and/or is designed to interact with a device for aerosol generation, also referred to as an aerosolizing device, preferably a nebulizer, for generating a liquid aerosol. A device for aerosol generation is a device that, depending on shape and use, can generate a mist, a cloud or droplet aerosol. The aerosolizing device is thereby preferably arranged near the cover region and in particular arranged in, above or below the cover region or cover, preferably at least inside or between the side walls when viewed in plan view. The device and/or the aerosolizing device are adapted such that the aerosol can be released in the direction of the base region. The aerosolizing device is arranged above the base region or can be arranged there in such a way, that the aerosolizing device at least partially covers the base region in a vertical plan view, and is preferably arranged approximately centrically thereto. The device preferably features suitable device for positioning and/or fastening the aerosolizing device. According to the invention, the sample can be wetted with a substance.

The positioning device allows for the positioning of in particular at least one sample, particularly a cell sample, and preferably epithelial cells, preferably located at the ALI. The positioning device is preferably plate-shaped and preferably has one or more recesses for the sample or the sample holder.

A preferred example of a positioning device is a microtiter plate. Further examples are petri dishes or object slides. The recesses of the positioning device are preferably formed to receive a nutrient medium for the cells as well as a positioning aid, in particular Transwell inserts, by means of which the cells can be arranged at the ALI.

The base region of the device can be designed to receive, or interact with, a positioning device. For this purpose, the base region is designed to laterally enclose or accommodate a positioning device. The base region may have a base plate which closes the base opening formed by the side walls entirely or at least partially. The positioning device may be arranged on the base plate. The positioning device can, for example, be designed as one, two, three, or more than three, microtiter plates. The base region is preferably designed to accommodate such a number of microtiter plates, preferably by a corresponding base plate, having a recess for placement of the microtiter plate which is adapted to the geometry of the side walls. This may be particularly advantageous since the stipulated [sic-should this be vorbeschriebene, i.e. "described above"?] device can then be used with existing systems. Preferably, these are microtiter plates. However, the positioning device can also be adapted. Preferably, the positioning device comprises elements for measuring and/or regulating temperature, preferably by means of a water circuit or an electrical temperature control device, for example a heater, elements for supplying the sample, e.g. with culture medium, and/or elements for measuring the weight of the deposited aerosol, preferably by means of one or more quartz crystal microbalance(s). Such a quartz crystal microbalance is preferably and particularly suited for direct, in situ (real-time) determination of the amount of test substance deposited on the sample. The positioning device is preferably designed to wet 6, 12, 24, 48, 96, 384 or 1536 samples, or 2×(6, 12, 24, 48, 96, 384 or 1536) or 3×(6, 12, 24, 48, 96, 384 or 1536) or 4×(6, 12, 24, 48, 96, 384 or 1536) samples.

The device described here allows for an aerosol to be deposited on a sample in a suitable and advantageous manner, and to be wetted. In particular, the device allows for rapid and homogeneous wetting of one or more samples in a simple and efficient manner. In particular, the structure of the device or the exposure chamber, and the positioning of the aerosolizing device in relation to the device as well as to the sample, prove to be advantageous. In particular, due to the aerosolizing device, the device allows for the formation of an aerosol cloud, in particular a cloud for which the laws of cloud motion at least generally apply. The device further allows the cloud to descend, preferably by the natural movement of the cloud, especially taking advantage of the cloud physical laws of motion and gravity, and thus allows the base region of the chamber, preferably the positioning device, and thus the sample, to be evenly wet in usually less than 3 min. Here, the device further allows the undisturbed descension of the cloud, in particular without a supplied or generated air flow (air stream-free or airflow-free) which would affect, for example, the movement of the aerosol, as is, for example, the case in the prior art. Advantageously, the aerosol is already generated airflow-free, i.e. without providing an air stream. Such an air flow is used in the prior art, for example, to generate the aerosol, for example by means of a nozzle or for transporting the aerosol past the sample and thus providing a partial removal of the aerosol. When transported airflow-free, the entire aerosol produced remains in the exposure chamber and can thus very efficiently deposit on the sample by means of gravity and an initial velocity of the cloud in the direction of the sample. An example of such airflow-free aerosolizing devices are known in the prior art as vibrating membrane nebulizers. It is preferred that the aerosolizing device be configured such that the departing aerosol has a certain initial velocity in the direction of the base region, which is different from zero.

The term cloud is herein preferably understood to mean that the rate of fall of the aerosol ensemble (under the influence of gravity) is higher than the rate of fall of the individual aerosols (or the diluted cloud) by at least one factor 10, and in particular because of the self-movement of the cloud, reaches a mean rate of fall of greater than 1 cm/sec, preferably greater than 3 cm/sec, most preferably greater than 10 cm/sec. Thus, preferably a slipstream effect appears in a cloud: at least some of the aerosol particles that are inside the cloud experience reduced air resistance since they fall in the slipstream of the outer or surrounding aerosol particles. This requires in particular, that the cloud is sufficiently dense. The aerosol particle volume for this purpose is at least $10^{-4}$%, preferably at least $10^{-3}$%, most preferably from $10^{-2}$% of the air volume in which it is contained.

In particular, the device can ensure that the aerosol is formed as a well-defined, intact cloud, preferably at least in the first 1 to 10 seconds of exposure, above and directly over the base region. The cloud can then descend without interference by, for example, objects mounted in the descension path, or, for example, by externally supplied, additional air streams in the device or the exposure chamber formed by it, wherein it is advantageous for the unrestricted descension of the cloud that the diameter of the cloud (perpendicular to the descending direction of the cloud) be significantly smaller than the clear span of the chamber at the respective height. It is particularly advantageous when the cross-sectional area of the exposure chamber is more than 2-fold, preferably 2.5-fold, most preferably more than 3-fold as large as the cross-sectional area of the cloud at the particular height, at least in the upper half of the chamber.

An exemplary embodiment provides that the cloud should have enough space to avoid being jammed, and thus be free to fall. This can, for example and in particular, be done by ensuring that the side walls of the chamber are placed far enough apart.

An exemplary embodiment provides that the cloud should arrive as an integral structure in the vicinity of the base region in order to be able to form a strong vortex for uniform spatial distribution of the aerosol in the exposure chamber. This may require that the drop height not be too large, as otherwise the cloud has widened too much and dissolved in the vicinity of the base region. If the drop height or the distance of the nebulizer unit outlet from the base region is too small, it is not possible for a sufficiently large vortex to form to be able to extend over the entire base region.

In particular, it is preferred that after departing from the aerosolizing device, the released aerosol particles be subject only to the effects of inertia and gravity, i.e. that no other external forces influence the cloud.

This and corresponding features of the device allow, in particular, the creation of a well-defined cloud with a strong "proper motion". For this, the following aspects can be advantageous: the diameter of the cloud, the liquid content of the cloud and/or the geometry of the exposure chamber, in particular its height and length/width. These parameters together preferably determine the rate of fall and the structural integrity of the cloud in the vicinity of the base region which are advantageous for forming a sufficiently strong vortex, and thus the uniform distribution of the aerosol as mist is [sic] in the exposure chamber. Thus, the mean rate of fall of the cloud can preferably be termed a result of the structural characteristics of the device. In particular, the rate of fall preferably decreases, the more the exposure chamber is filled with mist. The high rates of fall, therefore, preferably arise only at the beginning of the exposure process.

In particular, the (aerosol) cloud described herein can be defined by the fact that it has such a high liquid content, that it is visible in daylight. In contrast to the mist, a cloud is preferably localized, i.e. it is clearly bounded from an environment with low liquid content. As a result, the cloud moves like a higher density gas inside a gas with lower density, i.e. a cloud develops a strong proper motion due to gravity and thus a significantly higher rate of fall than the individual droplets would achieve alone. This occurs because inside the cloud, the droplets are protected from air resistance by the outer droplets and thus can fall faster ("slipstream effect", as previously mentioned). This cloud effect is advantageous for the invention presented here. In addition, a cloud that already has some initial velocity is slowed by the laws of friction, wherein a cloud as a geometric entirety is responsible for the sequence of movements (not the individual droplets). For uniform distribution of the aerosol on the base region, it is preferable and advantageous if the closely confined cloud is not directly deposited on the base region by inertial impaction, but instead the cloud is transferred by natural sedimentation into a uniform mist which fills the entire exposure chamber and then uniformly wets the base region or the samples contained inside the positioning device [sic] arranged therein. A mist is also a very dense liquid aerosol which differs from a cloud in that a mist is spread evenly and is widely spread, while a cloud is spatially limited, not necessarily distributed evenly, and has a sharp transition to the surrounding low-liquid air. A mist is produced in the device, for example and preferably, by the natural turbulence of the cloud when it hits the base region and is diverted there evenly to all sides, resulting in the formation of vortices or eddies which transfer the cloud to a uniform mist.

In particular, the mist described here can be described as a widely spread, evenly distributed liquid aerosol whose moisture content is so high that it is visible to the naked eye due to light scattering at the drops. Mist is spatially very stable; in contrast to a cloud, it does not develop a strong, intrinsic speed.

Furthermore, it is preferred and advantageous that the various elements of the device are dimensioned in a suitable manner, in particular in relation to each other. For example, the aerosolizing device, in particular its outlet, may be arranged approx. 5 cm to 50 cm, more preferably about 7 cm to 30 cm, and most preferably about 9 cm to 20 cm above the base region or the positioning device, and especially above the ALI. A vertical side length or height of the side walls is preferably about 8 cm to 53 cm, more preferably about 10 cm to 33 cm and most preferably about 12 cm to 23 cm. A preferred horizontal side length, or width of the base region and/or the side walls, is approximately 5 cm to 100 cm (especially when using several nebulizers, as described below), and more preferably about 7 cm to 50 cm, most preferably about 8 cm to 25 cm. The side walls may be equal in length and may feature a roughly square-shaped base region and/or cover region, or have different widths, and, for example, may include a rectangular base region and/or cover region. With side walls of varying lengths, the other preferred horizontal side length or depth of the base region and/or the side walls is about 4 cm to 80 cm (especially when using multiple nebulizers, as described below), preferably from about 5 cm to 40 cm and more preferably about 6 cm to 20 cm. The ratio between the vertical lengths (height) of the side walls to the horizontal side length (width, depth) is preferably about 1/1 to 2/1, and/or further preferred, about 4/3 to 1.5/1.

Further, it may be particularly preferred that the quotient between the area of the base region and the vertical extent of the side walls (in each case measured in $cm^2$ or cm) is between 3 and 12, preferably between 4-9, particularly preferably 5 and 7.5 (no unit listed).

Likewise, the quotient between the surface of the base region and the distance of the aerosolizing device inlet to the base region (in each case measured in $cm^2$ or cm) is between 3 and 12, more preferably between 4 and 9, particularly preferably between 5 and 7.5 (no unit listed).

Such dimensioning preferably permits an advantageous aerosol cloud formation and an effective, uniform and rapid wetting of the sample.

For forming a uniformly distributed mist out of the proper motion of the cloud throughout the exposure chamber, it is advantageous that the initial cloud (the cloud that is formed within the first few seconds of exposure, i.e. particularly within the first 10 seconds, preferably within the first 5 seconds, and particularly preferably within the first 3 seconds of cloud formation) meet the base region as a compact structure in order to have enough momentum to form a vortex which then spreads evenly over the entire base region. This entails preferably that the inlet of the aerosolizing device is positioned above the base region by no more than about 50 cm, preferably not more than 30 cm, particularly preferably not more than 20 cm.

In particular, it is preferred and advantageous when the distance between the opposing side walls is adjusted such that the vortices evenly fill the entire area of the base region thereby defined. This limits the preferred, maximum horizontal extent of the exposure chamber to preferably a maximum of about 10 times the diameter of the initial cloud situated at the entry point in the exposure chamber. This initial diameter of the cloud can, for example, be approximately 2 cm.

According to a preferred embodiment, the geometry of the cover region essentially corresponds to that of the base region and is vertically arranged thereto in the direction of gravity, above the base. The cover region can essentially extend along or in the vicinity of the imaginary plane which is defined by the (upper) ends of the side walls and/or is delimited to the outside by the side walls. Accordingly, the base region essentially extends along or near the imaginary plane defined by the (lower) ends of the side walls and/or is delimited to the outside by the side walls.

Furthermore, the base region and/or the cover region is/are essentially horizontal. This preferably and advantageously affects not only the simplicity of the design and manufacture but also the functionality of the device described above and below.

While the side walls which, as described, delimit the base and/or cover regions on the side, can be arranged essentially perpendicular, they are alternatively and preferably formed essentially as pyramid-shaped and/or conical, opening downwards or expanding.

The dimensions discussed herein and parameters of the device are preferably designed in such a way, and preferably aligned in such a way, that the described functionalities are preserved and/or enabled. For example, it is of an advantage that the aerosolizing device generates an aerosol, such that it forms a cloud. This aerosol cloud formed by the aerosolizing device can preferably essentially descend freely, in particular so that the resulting, powerful proper motion of the cloud leads to the formation of a pronounced vortex when it impinges upon the base region. For this purpose, it is advantageous that the aerosolizing device, the cloud and/or the device is/are configured such that the cross-sectional area of the cloud (perpendicular to the direction of descension of the cloud) is significantly smaller than the clear span of the chamber at the respective height, in particular that the cross-sectional area of the exposure chamber at least in the upper half of the chamber is more than two-fold, preferably 2.5-fold, more preferably more than 3 fold, as large as the cross-sectional area of the cloud at the respective height.

The cover region may, apart from the respective end portions of the side walls, merely be formed as an opening or recess. However, it is particularly preferred that the cover region have a cover wall. This can further shield the area that is separated from the environment by the vertical side walls, also referred to as the exposure chamber.

The cover wall may be designed to be detachable or may be detachably mounted to the side walls. Alternatively, it can be formed integrally with the side walls. Particularly preferably, the cover wall may also feature a recess or an opening, or may have an area that is detachable or designed to be opened. This removable area or this opening of the cover wall is particularly preferably designed or dimensioned such, that the aerosolizing device can conduct the aerosol through this area or opening into the exposure chamber, vertically downwards toward the base region. The aerosolizing device can hereby be arranged vertically just above the cover region, exactly at the height of the cover region or vertically just below the cover region. The position of the aerosolizing device is thereby determined preferably by its aerosol outlet, preferably by the site of the aerosol generation, for example, the vibrating membrane. The positioning of the aerosolizing device can lead to a particularly suitable and advantageous cloud formation.

Furthermore, the side walls can be at least partially transparent. For example, the side walls can feature or is formed of glass and/or plastic, for example, of a transparent polycarbonate, preferably Macrolon. The latter is particularly advantageous as it can easily be sterilized with, e.g., alcohol. Furthermore, it may be possible for the user to observe phenomena that take place within the device. In particular, a user may hereby be in the position to observe the extent to which a cloud and vortex formation and/or wetting has progressed. This primarily serves for quality control and the optimization of the procedure.

Furthermore, the device can hereby be designed relatively light (lightweight). For example, the device may be designed such, that its total weight (e.g. without the positioning device) is no more than five kilograms, preferably no more than one kilogram, for example, about 800 grams (the positioning device hereby preferably comprises no additional, weight-relevant features, such as a heating device). Using the light design and also the suitable dimensioning described above, such a device can in particular be used in a laminar flow cabinet or sterile chamber.

The cover wall can feature at least one of the materials which comprise the side walls. In terms of manufacturing, this can be especially easy to realize. Further, this results in a uniform appearance of the device.

The device and particularly its components, such as the side walls, can be designed to be outwardly air-tight and gas-tight Such a device is also particularly suitable for toxicological experiments or for the study of toxicological substances. In particular, the components in such an arrangement (for example, the side walls) can accordingly be sealed air-tight or gas-tight against each other, for example, by using sealing materials.

The aerosolizing device can be designed as a nebulizer. Furthermore, the aerosolizing device may have a plurality of nebulizers which are suitably arranged to one another. The nebulizers can thereby be arranged preferably close together or closely spaced, in particular so that the respective aerosol clouds generated by the nebulizer merge to a large cloud shortly after generation. Alternatively and/or additionally, the nebulizers of the aerosolizing device can preferably be arranged so far apart that each nebulizer generates a separate cloud, wherein the individual aerosol clouds merge only after descending and swirling into a mist that allows a uniform droplet deposition. For this, the spatial arrangement of the nebulizers is in particular important, which can in turn depend on the geometry of the chamber, the active cross-sectional area (diameter) of the initial cloud, and the liquid discharge rate of the nebulizer.

The vibrating membrane nebulizers may, for example, feature a diaphragm which is preferably aligned parallel to the horizontal. An aerosolizing device designed in such a way may particularly ensure a suitable cloud formation, as described above.

In particular, the aerosolizing device is preferably adapted to produce or release aerosol particles having an average size between about 1 μm and 15 μm, more preferably between about 2 μm and 10 μm, and most preferably between about 3 μm and 7 μm. This also preferably positively affects a suitable cloud formation and the sedimentation of the mist. Excessively large drops directly impact during the approach of the initial cloud to the base region. Since the initial cloud is not evenly distributed over the base region, this would lead to a non-uniform wetting of the base region. Droplets that are too small do not have enough mass to efficiently sediment on the base plate, which would prolong the sedimentation time and thus the time of exposure, and would reduce the deposition efficiency.

Preferably, the aerosolizing device is, particularly in a vertical plan view, arranged centrically over the base region or the positioning device. Here, in a vertical plan view direction, the center of the base region or the positioning device preferably roughly coincides with the center of the aerosolizing device. If the aerosolizing device comprises several nebulizers, these are preferably arranged essentially symmetric to the center of the base region or the positioning device. [sic] This may particularly promote the cloud formation occurring symmetrically and uniformly so that the sample is wetted particularly uniformly with the substance.

According to a further preferred embodiment, the device features a light source. This is preferably adapted or arranged to indicate to a user as to whether the cloud has already fully descended in the exposure chamber. For example, the light source may be a laser source, such as a laser pointer. The light source is preferably arranged such, that a defined light beam is emitted into the chamber. Preferably, a beam is generated with a diameter which is smaller than 1 cm. Preferably, the arrangement is such that the emitted laser beam runs essentially perpendicular to the line of sight of the user. In this way, the user can on the one hand be protected against the laser radiation. On the other hand, the user only recognizes the laser beam as such if it is scattered—for example, in fine particles in a cloud or in a mist. Such a light source thus provides a simple and safe possibility of observing if the cloud or mist are still present, or whether the aerosol has already settled on the sample. In other words, such a light beam is invisible to the operator of the device (who, for example, looks into the chamber from the "front"), unless the chamber contains a sufficiently dense cloud or sufficiently dense mist, whose droplets are scattered with light in all directions, i.e. also to the front. As soon as the light beam is no longer visible, the cloud has completely descended to the base region and the wetting of the sample can be considered complete. Preferably, such a light source is arranged on a side wall in such a way, that the beam extends perpendicularly through the side wall, more preferably at a horizontally centered position of the side wall. Vertically, it is particularly preferable that the light source is arranged at a distance between about 5 and 8 cm above the positioning device. Overall, a simple and user-friendly control can be provided this way to see whether the cloud has already completely descended to the base region in the chamber and thus, the wetting process is completed. This is advantageous in comparison to a purely visual inspection.

It is also preferred that the device further comprises a control chamber which is separated from the exposure chamber, for example, by at least a wall, such that the aerosol generated by the aerosolizing device does not enter the control chamber. In this way, in addition to the samples which are wetted by the aerosol, samples can also be provided that do not experience such wetting but are otherwise exposed to the same influences. Such samples can be used for comparative purposes or as controls particularly for biological samples in order to ensure that the handling of the biological samples does not have a(n)(unintentional) biological effect on the samples.

According to an exemplary embodiment, the invention also relates to a method for wetting at least one sample with an aerosol. In particular, this method can be carried out using a device such as the one described above. It preferably further comprises the steps or functionalities described in connection with the above discussion of the device.

The method preferably includes the steps of providing at least one sample, generating and providing an aerosol cloud above, preferably vertically above, the at least one sample, and the descension of the aerosol cloud in the direction of the sample.

Preferably, as it approaches the base region, the cloud forms at least one vortex and is converted into a mist. This mist then descends toward the sample.

The aerosol particles are thereby released via the airflow-free aerosolizing device with a certain exit velocity (or initial velocity), preferably in the direction of the sample or the positioning device.

The aerosol cloud drops, preferably gravitationally, and due to the exit velocity of the cloud from the nebulizer. The cloud thus preferably descends freely. Then, the cloud is preferably deflected in the base region, for example, at the sample and/or the positioning device. The deflection takes place preferably uniformly, laterally in all directions, and the cloud then again changes direction to move upwards via deflection at the sidewalls. This creates preferably uniform vortices or eddies which particularly lead to a uniform distribution of the aerosol cloud and thus form an aerosol mist, especially in the lower part of the exposure chamber. In particular with progressing nebulization, the device fills gradually with mist from the base up. Due to gravity, this mist is most dense at the base or close to the base. After that, especially after completion of nebulization, the mist drops to the positioning device and to the at least one sample arranged thereupon. The samples are, regardless of where they are located on the positioning device, evenly wetted. The time from the start of nebulization to the conclusion of the, particularly uniform, wetting, is preferably less than 12 min, more preferably less than 6 minutes, most preferably less than 3 min.

The samples are, as described above, cultured cells, preferably epithelial cells, which are preferably arranged or cultured at the ALI. They are particularly arranged on a standard microtiter plate. Similarly, they could also be made up of other biological material, for example, tissue, bacteria or the like. A realization of samples as samples of material is also possible. Preferably, the aerosol and thus the cloud or the mist feature a pharmaceutically and/or toxicologically effective substance.

The aerosol can have a liquid substance which is, for example, pipetted into the aerosolizing device. The generated aerosol cloud is preferably such, in particular so dense (high liquid content), that the laws of cloud motion apply, wherein preference is given to the parameters described above for the cloud properties. This in particular leads to the cloud descending due to its exit velocity from the nebulizer and its gravitational force (i.e. by descending). As it approaches the base region, it forms vortices that transform the cloud into a mist which then evenly descends to the base region and the sample located there via gravity.

The expert will understand that the above-described aspects which have been described in detail in connection with the inventive device, are also realized in the inventive method.

Alternatively and/or additionally, the present invention comprises the following exemplary embodiments:

The device (2) for wetting at least one sample by an aerosol, wherein the device (2) comprises: side walls (4a, 4b, 4c, 4d); a base region (6) bounded by the side walls (4a, 4b, 4c, 4d); wherein the base region (6) is adapted for receiving, or for interacting with, a positioning device (8) for positioning the sample(s) that is/are placed, for example, in recesses (18), a cover region (10) which sits vertically opposite the base region (6), and is delimited by the side walls (4a, 4b, 4c, 4d), wherein the device (2) forms an exposure chamber (12); and an aerosolizing device (14) for generating an aerosol (16) which is located in the vicinity of the cover region (10), wherein the aerosolizing device (14) is arranged above the base region (6) in such a way that the aerosolizing device (14) covers the base region (6) at least partially when viewed in a vertical plan view.

The device (2) for wetting at least one sample by means of an aerosol, wherein the device (2) comprises side walls (4a, 4b, 4c, 4d), a base region (6) bounded by the side walls (4a, 4b, 4c, 4d), wherein the base region (6) is adapted for receiving or for interacting with a positioning device (8) for positioning the sample, a cover region (10) which is vertically opposite the base region (6), and which is bounded by the side walls (4a, 4b, 4c, 4d), wherein the device (2) forms an exposure chamber (12), and an aerosolizing device (14) for generating an aerosol (16) which is located preferably in the vicinity of the cover region (10), wherein the device (2) and/or the aerosolizing device (14) are designed to form an aerosol cloud.

The device (2) for wetting at least one sample by means of an aerosol, wherein the device (2) comprises: side walls (4a, 4b, 4c, 4d), a base region (6) bounded by the side walls (4a, 4b, 4c, 4d), wherein the base region (6) is adapted for receiving or for interacting with a positioning device (8) for positioning the sample(s) which is/are, for example, placed in recesses (18), a cover region (10) which is vertically opposite the base region (6) and is bounded by the side walls (4a, 4b, 4c, 4d), wherein the device (2) forms an exposure chamber (12), and an aerosolizing device (14) for generating an aerosol (16), preferably arranged in the vicinity of the cover region (10), wherein the aerosolizing device is designed as an airflow-free aerosolizing device.

In an embodiment, the device has no aerosolizing device but instead is designed to receive or interact with such.

In an embodiment, the aerosolizing device (14) can be arranged above the base region (6) in such a way that the aerosolizing device (14) at least partially covers the base region (6) in a vertical plan view.

In an embodiment, the side walls (4a, 4b, 4c, 4d) can be essentially vertical, and/or wherein the base region (6) is essentially horizontal, and/or wherein the base region (6) is bounded laterally by the side walls (4a, 4b, 4c, 4d), and/or wherein the cover region (10) is bounded laterally by the side walls (4a, 4b, 4c, 4d).

In an embodiment, the aerosolizing device (14) can be adapted to release the aerosol in the direction (R) of the base region (6).

In an embodiment, the aerosolizing device (14) can be arranged in a vertical plan view inside or between the side walls (4) and preferably has a suitable minimum distance from the side walls, preferably at least 3 cm.

In an embodiment, the aerosol features a liquid and/or a solid, and comprises preferably liquid and/or solid airborne particles and a gas.

In an embodiment, the device (2) and/or the nebulizer (14) are designed to form a cloud.

In an embodiment, the device is adapted to be operated without an external air flow, more particularly airflow-free.

In an embodiment, the aerosolizing device comprises at least one nebulizer and preferably features a nebulizer designed as an airflow-free nebulizer, and preferably features a vibrating membrane nebulizer, and preferably is one.

In an embodiment, the aerosolizing device (14) is oriented such that the initial direction of the cloud movement forms an angle of less than 30° with the vertical and preferably is essentially aligned parallel to the vertical, and the aerosolizing device (14) preferably having a perforated membrane which forms an angle of less than 30° with the horizontal, and which is preferably aligned essentially parallel to the horizontal.

In an embodiment, wherein in a vertical plan view, the aerosolizing device can be arranged approximately centered above the base region or the positioning device.

In an embodiment, device can be designed such that a cloud initially produced by the nebulizer is such that the mean rate of fall of the cloud generated at the beginning of the exposure is greater than 1 cm/s, preferably greater than 3 cm/s, particularly preferably greater than 10 cm/s, wherein said velocity is preferably the exit velocity of the cloud exiting the aerosolizing device.

In an embodiment, the device can be designed such that the cloud generated by the aerosolizing device is such that the cloud can freely descend and that therefore, a rapid transport of the aerosol to the base region is guaranteed.

In an embodiment, the exposure chamber is dimensioned such that the horizontal cross-sectional area of the exposure chamber in the upper half of the chamber is more than 2-fold, preferably 2.5-fold, most preferably more than 3 times as large, as the cross-sectional area of the cloud.

In an embodiment, a positioning device (8) can be provided for positioning a sample.

In an embodiment, the device and/or the positioning device is/are designed to receive or wet cells, and more preferably epithelial cells, that are used as a sample in, for example, recesses (18).

In an embodiment, the device and/or the positioning device is/are adapted such that the sample can be arranged as an air-liquid interface (ALI)

In an embodiment, the positioning device features elements for measuring and/or regulating a temperature, for example an electric heater or a temperature control device operated with the aid of a water circuit, elements for supplying the sample, for example, with nutrient medium, and/or elements for measuring the weight of a substance deposited one or more samples, for example one or more quartz crystal microbalances.

In an embodiment, the aerosolizing device, particularly its outlet, can be arranged between 5 cm and 50 cm vertically above the base region or the positioning device, preferably between 7 cm and 30 cm, more preferably between 9 cm and 20 cm, and in particular at approximately 16 cm.

In an embodiment, the aerosolizing device, preferably the vibrating membrane of a nebulizer, can be arranged vertically above the cover region, for example, between 0 cm and 10 cm, more preferably between 3 cm and 7 cm and in particular approximately 5 cm above.

In an embodiment, the aerosolizing device can be arranged vertically below the cover region, preferably between 0 cm and 10 cm, more preferably between 3 cm and 7 cm and in particular approximately 5 cm below.

In an embodiment, the side walls can be at least partially transparent.

In an embodiment, the side walls can be made of glass and/or plastic, for example polycarbonate, and particularly preferably at least portions of the side walls feature such a material or formed of such a material.

In an embodiment, the side walls can have a vertical expansion between 8 cm and 53 cm, preferably between 10 cm and 33 cm, most preferably between 12 cm and 23 cm, and particularly approximately of 19 cm.

In an embodiment, the base region can feature a first horizontal side length between 5 cm and 100 cm, preferably between 7 cm and 50 cm, most preferably between 8 cm and 25 cm, and a second horizontal side length between 4 cm and 80 cm, preferably between 5 and 40 cm, most preferably between 6 cm and 20 cm.

In an embodiment, the base region can be designed exactly for receiving a positioning device which comprises one, two, three or four microtiter plates.

In an embodiment, the device can be designed for the uniform wetting of numerous samples, preferably of 6, 12, 24, 48, 96, 384 or 1536 samples, or 2×(6, 12, 24, 48, 96, 384 or 1536) or 3×(6, 12, 24, 48, 96, 384 or 1536) or 4×(6, 12, 24, 48, 96, 384 or 1536).

In an embodiment, the cover region and/or the device have a cover wall in the cover region can extend essentially horizontal.

In an embodiment, the cover wall can be detachably arranged on the vertical side walls or connected therewith, and/or features an opening or a recess and/or an area which is designed to be opened.

In an embodiment, the removable region or the opening are designed or dimensioned in such a way that the device can be cleaned internally and the sample(s) can be placed on the base region.

In an embodiment, a further, detachable portion or an opening is essentially positioned centrically in the cover region.

In an embodiment, the further detachable region or the opening are designed or dimensioned such, that the aerosolizing device can conduct the aerosol into the exposure chamber.

In an embodiment, the cover wall includes at least one of the materials that comprise the side walls.

In an embodiment, the vertical distance of the aerosolizing device, particularly its outlet, is between 5 cm and 50 cm, preferably between 7 cm and 30 cm and most preferably between 9 cm and 20 cm, particularly approximately 16 cm from the sample, and preferably from the air-liquid interface that is represented by a biological sample.

In an embodiment, the device features exactly one nebulizer.

In an embodiment, the device comprises a plurality of nebulizers.

In an embodiment, the aerosolizing device is adapted to produce and/or release aerosol particles with an average aerodynamic diameter between 1 μm and 15 μm, preferably between 2 μm and 10 μm, most preferably between 3 μm and 7 μm.

In an embodiment, a laser source which is designed and positioned to emit a laser beam through at least one side wall, essentially parallel to the horizontal and perpendicular to the operator's line of sight, so that the laser beam is visible to the user precisely when a cloud or mist is present in the exposure chamber.

In an embodiment, the device further comprises a control chamber which is isolated from the exposure chamber by preferably at least one wall so that the aerosol generated by the aerosolizing device does not enter the control chamber.

Method for wetting at least one sample by means of an aerosol, in particular with a device according to any one of the preceding aspects, said method comprising the steps of: providing at least one sample, generating an aerosol cloud (16) above, preferably vertically above, the at least one sample at a position that at least partially covers the base region (6) in a vertical plan view and allowing the aerosol cloud to descend in the direction (R) of the sample.

A method for wetting at least one sample by means of an aerosol, in particular with a device according to any one of the preceding aspects, said method comprising the steps of providing at least one sample, generating an aerosol cloud (16) and allowing the aerosol cloud to descend in the direction (R) of the sample.

A method for wetting at least one sample by means of an aerosol, in particular with a device according to any one of the preceding aspects, said method comprising the steps of providing at least one sample, generating an aerosol (16) by means of an airflow-free nebulizer, and allowing the aerosol to descend in the direction (R) of the sample.

In an embodiment, provided is a step of forming vortices that transform the cloud into a mist which uniformly fills the exposure chamber in a vertical plan view of the base region.

In an embodiment, provided is a step of gravitational descension of the mist.

In an embodiment, provided is a step of generating the aerosol comprises generating an aerosol cloud.

In an embodiment, the step of generating the aerosol (16) or the step of generating the aerosol cloud takes place vertically above the at least one sample at a position that at least partially covers the base region (6) in a vertical plan view.

In an embodiment, provided is a the step of spatially and uniformly wetting the at least one sample.

In an embodiment, provided is a step of generating the aerosol (16) above the at least one sample.

In an embodiment, provided is a step of forming vortices in the aerosol cloud, preferably by the cloud impinging on the sample and/or a positioning device (8) which provides the sample.

In an embodiment, provided is a step of forming a mist and the gravitational descension of the mist on the at least one sample.

In an embodiment, provided is a step of uniform wetting that when using a positioning device for more than one sample with a maximum size of 5 cm², the samples are coated with approximately the same substance mass, wherein the mass variability about the mean of the samples, particularly the 95% confidence level, is less than 40%, preferably less than 30%, more preferably less than 20%, and most preferably less than 10%.

In an embodiment, provided is a step of providing a sample on a positioning device, preferably at the ALI.

In an embodiment, provided is an aerosolizing device (14), preferably an airflow-free nebulizer, to generate the aerosol (16).

In an embodiment, the aerosol features a pharmaceutically active substance or a toxic substance such as water-soluble inorganic and/or organic substances, peptides and/or proteins.

In an embodiment, the aerosol features naturally occurring or intentionally generated nanoparticles and/or airborne particles of inorganic and/or organic substances, for example, soot, metal and metal oxide particles, carbon nanotubes, liposomes, and/or gelatin particles.

In an embodiment, a uniform wetting of the sample is achieved in less than 12 min, preferably in less than 6 min, most preferably in less than 3 min.

The method steps can occur, but not necessarily, in the order described.

The present invention, that is, the present inventive device and the inventive method, enable fast, efficient and uniform wetting or coating of samples, preferably cells at the air-liquid interface (ALI), with an aerosol, in particular with liquid aerosols, further particularly with liquid aerosols with pharmaceutical substances. By transporting the substances in an aerosol as described above via cloud convection, particularly without generating or using an external air flow into or out of the device, or without inertial impaction or spraying, disadvantages of the prior art may be prevented and advantages realized. Thus, in the present invention, a relative air humidity of an almost constant, approximate 100% can be achieved without great technical effort, which can lead to good culturing conditions for cells, a significantly slowed or completely prevented evaporation of the droplets, and a large droplet deposition efficiency (between 70 and 95% at the base region). This can be achieved in particular by the water content in the cloud being so high that the evaporation of proportionally small amounts of liquids (<5%) already results in saturated conditions. The present invention makes it possible, in particular, to forego a complicated, expensive and error-prone humidity control system. A further advantage of the present invention is that no active homogenization of the aerosol is necessary. In known systems, such an aerosol must be obtained through, for example, active mixing, for example, with a ventilator. That is not necessary here because a homogeneous and uniform distribution can be achieved with the use of cloud physical effects.

Furthermore, for example, the rapid deposition duration of preferably less than twelve minutes up to less than three minutes ensures that the sample does not need to dwell long in the exposure chamber. This can be particularly advantageous especially in biological systems, for example in cells, as these are very sensitive to changes in their environment. This high sensitivity is, especially at longer exposure times, the justification for using a thermostatization of the system.

The present invention outperforms the known systems in particular both in terms of efficiency, dose accuracy and equal distribution of substances with a significantly improved ease of handling.

It is further preferred that the device can be operated aseptically. For example, the accessible design, the small number of structural components as well as the use of alcohol-persistent materials allow for easy sterilization of all aerosol and cell-exposed surfaces. Moreover, the device is compact enough to fit into commercially available laminar flow cabinets. This is an advantage as compared to most known systems.

In particular or summarized it can be said, especially as compared to previous systems, that the present invention advantageously provides an airflow-free system, i.e. in particular without air intake and outflow, with very short exposure times (of less than 3-12 minutes instead of several days or hours, or at least 30 min in the prior art) with comparatively high substance transport (about 0.5 µl substance per $cm^2$ sample per minute) to the samples, which allows for a high sample throughput. Only a slight, if any, intervention is required, e.g. in respect of $CO_2$ supply of the temperature control for handling the cells outside the incubator, etc. Also, unusually high deposition efficiencies are achieved (more than 70%, preferably about 75-95%, and more preferably almost 100% of the aerosol reaches the base region that contains the sampling device with the samples) which have a high degree of reproducibility with repeated application, with a deviation of 25%, preferably 20%, and most preferably 10% of the medium dose (95% confidence level), with a simultaneously high uniform distribution of the deposited aerosol on the sample(s). The variability of the dose about the mean (95% Confidence Level) in 6 Transwell inserts of a 6-well microtiter plate is less than 40%, preferably less than 30% and most preferably less than 20%. A completely sterile procedure for further culturing or repeated exposures is also possible. In addition, the system can be modular in design and can be easily supplemented when necessary with additional components, e.g. a heater, a (quartz crystal) microbalance, a laser beam or the like. A particularly good applicability for biological samples is achieved in particular by the low exposure time and low stress due to the gentle method of the aerosol deposition (slow "cloud deposition").

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 illustrates an embodiment of a device for wetting at least one sample with aerosol;

FIG. 2 illustrates an embodiment of a device for wetting a positioning device with up to six samples with an aerosol, FIGS. 3a-3c show steps of a method with a device for wetting a positioning device with up to six samples with an aerosol.

DETAILED DESCRIPTION

Figure 4:
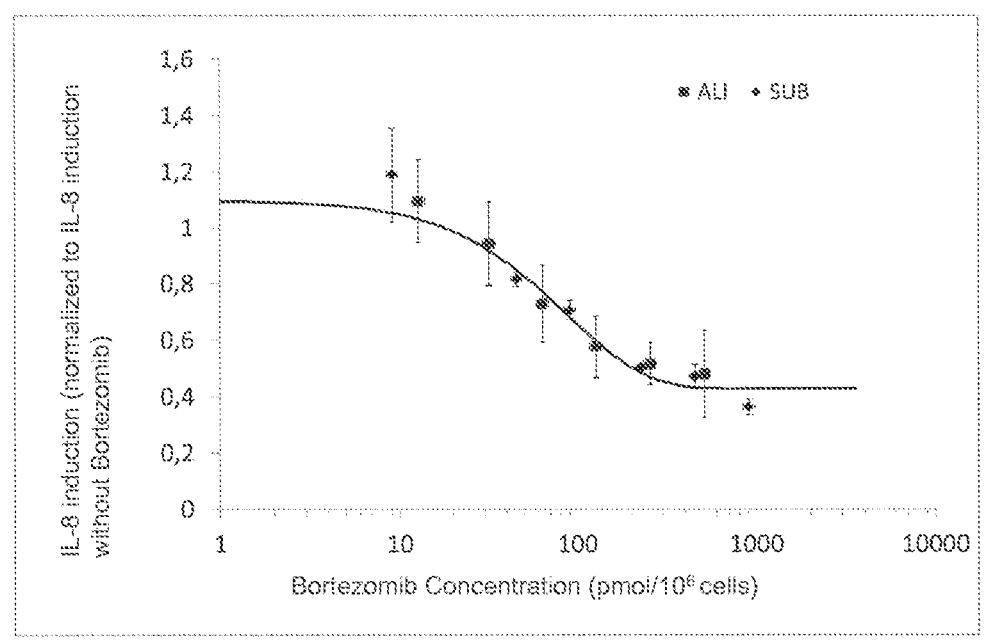
FIG. 4 illustrates the dose-dependent anti-inflammatory effect of the proteasome inhibitor Bortezomib on a human, non-polarized, pulmonary cell line (A549) at the ALI, stimulated with a tumor necrosis factor α (TNFα) in an inflammatory manner.

Below, an exemplary device and an exemplary method are exemplified. FIG. 1 shows a first embodiment of a device 2 for wetting at least one sample with a substance. The device 2 essentially features vertical side walls 4a, 4b, 4c and 4d. In the illustrated form, these essentially vertical side walls 4a, 4b, 4c and 4d essentially form right angles to each other. Although this is preferred, it is not necessary. Alternatively, it is possible that device 2 has a different number of essentially vertical side walls 4a, 4b, 4c and 4d. For example, it is conceivable that only three side walls are provided, which each form between them an angle of about 60°. Likewise, more than four side walls can be provided, for example, 5, 6, etc. It is also conceivable that only one continuous wall is provided, for example in the form of a cylinder. The angles between the vertical side walls 4a, 4b, 4c and 4d can also vary. Finally, it may be preferred that the side walls are not essentially vertical and, for example, form a truncated pyramid or cone which preferably taper upwards.

Furthermore, the device 2 features an essentially horizontal base region or substructure 6 which provides the space for positioning at least one sample. This is preferably bounded by the side walls 4a, 4b, 4c and 4d, or their lower ends. The base region or substructure 6 illustrates a functionalizable base region. In one embodiment, as shown in FIG. 1, this base region, apart from the lower regions of the side walls 4a, 4b, 4c and 4d, features no substance or matter—i.e. the entire base region 6 can be realized as a recessed area, or is designed as a, in particular, laterally delimited opening bounded by the side walls. Alternatively, the base region may comprise a bottom plate or other elements, not shown. The device 2 further includes a cover region 10. Here, this cover region 10 lies vertically opposite to the base region. The cover region 10 is also preferably bounded by the side walls 4a, 4b, 4c and 4d. Like the base region 6, the cover region 10, apart from the upper portions of the side walls 4a, 4b, 4c and 4d, may not feature any matter or substance. In other words, the cover region 10 may thus be formed as a recessed area or be designed as a laterally delimited opening bounded by the side walls. It is preferable that the cover region 10 not be completely formed as a recessed portion. This way, the cover region 10 can also feature material, for example, a cover. In such a case, however, the cover region 10 is provided with a recess or an opening which is preferably arranged in the middle of cover region 10 to connect the nebulizer. This opening or recess may also be designed as lockable.

The vertical side walls 4a, 4b, 4c and 4d and the base region 6 and cover region 10 essentially partition off a spatial area which forms an exposure chamber 12. This can have an essentially square or rectangular base region. Other shapes may be preferred. The illustrated embodiment further features an aerosolizing device, here a nebulizer 14, to produce a gas-matter mixture. This aerosolizing device 14 is arranged in the vicinity of the cover region 10. In other words, the aerosolizing device 14 is spaced at approximately the same distance from the base region 6 as from the cover region 10.

The nebulizer 14 is adapted to release aerosol in the direction of the base region 6, as described hereinafter. Furthermore, the aerosolizing device 14 is arranged above the base region 6 in such a way that the aerosolizing device 14 at least partially covers the base region 6 in a vertical plan view and is preferably located centrically thereto.

The base region 6 is adapted for receiving a plate-like positioning device 8 for positioning the sample(s). This can, for example, be implemented by a suitable design and dimensioning of the base region 6. In FIG. 2, a preferred embodiment is shown which also depicts the plate-like positioning device 8 for up to six samples that are arranged in the recesses or depressions 18. These depressions 18 can contain the samples and/or the sample holders. Here, the device or its base region 6 can be pulled or placed on the positioning device. Alternatively, the base region features a, preferably detachable, base, on which the positioning device can be arranged or which is designed as a positioning device.

The aerosol features solid and/or liquid, preferably liquid, aerosol particles. It is still particularly preferred that the aerosol contain a pharmaceutical or toxic substance.

Typically, the aerosolizing device, particularly its outlet into the exposure chamber, is spaced vertically at a distance D from the positioning device and in particular from the samples (FIG. 2). This distance D may be, for example, between about 5 cm and 50 cm, preferably between about 7 cm and 30 cm, most preferably between approximately 9 cm and 20 [sic].

Accordingly adapted, the vertical side walls 4a, 4b, 4c and 4d typically have a vertical extension L (FIG. 1) between about 8 cm and 53 cm, most preferably approximately between 10 cm and 33 cm, and in particular between 12 cm and 23 cm.

The horizontal extent H1 and H2 of the side walls 4a, 4b, 4c and 4d, and thus the lateral length of the base region 6 for positioning the positioning device 8, may be designed in such a way that a first horizontal side length H1 ranges between 5 cm and 100 cm, preferably between 7 cm and 50 cm, and most preferably between 8 cm and 25 cm, and a second horizontal side length H2 ranges between 4 cm and 80 cm, preferably between 5 cm and 40 cm, and most preferably between 6 cm and 20 cm.

Typically, the dimensioning is configured such that the base region 6 is designed to receive one, two, three or four microtiter plates. This way, the positioning device 8 as shown in FIG. 2 can in particular have one, two, three or four microtiter plates and can have in particular of one, two, three or four microtiter plates. It is particularly preferred that the device 2 and in particular the distance of the essentially vertical side walls 4a, 4b, 4c and 4d be designed in such a way that precisely a great number of such standard microtiter plates can be evenly arranged inside the side walls 4a, 4b, 4c and 4d.

Further, the device 2, and in particular the dimensioning and the positioning device 8, may be configured such that they are suitable for wetting a plurality of samples, preferably as previously described. In FIG. 2, such an embodiment is shown in which the device is designed for wetting a maximum of 6 samples.

It is particularly preferable that the sample comprises cells, preferably epithelial cells. Therefore, the device 2 is particularly preferably suited to wet these cells or epithelial cells. Furthermore, it is particularly preferred that the positioning device 8 is adjusted such that the samples, e.g. the cells and preferably, the epithelial cells, form an air-liquid interface (ALI). Preferably, a positioning device features recesses in which cell samples can be arranged for ALI culturing via inserts, for example, Transwell inserts.

According to the illustration, the aerosolizing device 14 is arranged in the vicinity of the cover region 10. In other words, the aerosolizing device 14 sits roughly at an equal distance to the base section 6 or to the positioning device 8, as does the cover region 10.

The aerosolizing device 14 can hereby be arranged, for example, just above the cover region 10 or just below the cover region 10—for example, at a distance between 0 cm and 10 cm, preferably between 3 cm and 7 cm and in particular approximately 5 cm above or below.

It is particularly preferred that the device 2 features exactly one aerosolizing device 14. However, the invention can also be realized having more than one aerosolizing device 14, e.g. with 2, 3, 4 or 5 aerosolizing devices 14 (not shown).

It is particularly preferred that the aerosolizing device 14 have a vibrating membrane and preferably is one. The aerosolizing device 14 is typically a perforated (vibrating) membrane which is primarily aligned parallel to the horizontal. Typically, the aerosolizing device 14 is adapted to generate or release aerosol particles of an average size between 1 µm and 15 µm, preferably between 2 µm and 10 µm, most preferably between 3 µm and 7 µm.

Furthermore, it is preferred that the aerosolizing device 14, in particular in plan view, is arranged approximately centered over the base region 6 and the positioning device 8.

In particular, the positioning of the aerosolizing device 14 in the area or the vicinity of the cover region 10 allows the aerosol 16 to be released without an additional air stream and to be introduced into the exposure chamber. In other words, the precise arrangement of the aerosolizing device 14 allows for the aerosolizing device 14 to at least partially cover the base region 6 or the plate-like positioning device 8 in a vertical plan view. This in turn allows the aerosol 16 to leave the aerosolizing device 14 at a speed which is fast enough to quickly and contiguously transport the cloud to the vicinity of the base region, but not so fast that the aerosols impact there, right at the first approximation to the base region. In particular, the released liquid particles can exit the aerosolizing device 14 with a mean velocity of between about 5 cm to 1000 cm/s, preferably about 10 to 500 cm/s, particularly preferably between 30 and 130 cm/s. It is particularly preferred that after leaving the aerosolizing device 14, the released aerosol particles are subject to nothing more than the effect of inertia and gravity, i.e. that no other external forces are applied to the cloud. After exiting, the aerosol particles preferably form an aerosol cloud, as described above. An additional air stream is preferably not necessary.

The device preferably has 3 parts (FIG. 1 or 2). Namely a (standard) microtiter plate as positioning device, in which the samples (cells) are cultured, a vibrating membrane to generate an aerosol cloud, preferably of droplets, and an exposure chamber, as described above.

Preferably, the cuboid exposure chamber is designed in plan view in such a way that exactly one standard microtiter plate fits inside (12.8 cm×8.6 cm). The chamber is about 16.0 cm high and has a commercially available vibrating membrane nebulizer centrically mounted on its cover (the height above the chamber cover is here preferably about 5 cm) which turns a liquid directly into a dense aerosol or droplet cloud by means of a vibrating, perforated membrane. The nebulizer is directed downward so that the cloud is formed directly above the standard microtiter plate. The chamber includes transparent polycarbonate (Macrolon) which can easily be sterilized with alcohol. The whole system is very compact with a total weight of about 0.8 kg.

With reference to FIGS. 3a-3c, in the following a method for wetting at least one sample with an aerosol is exemplified, in particular by means of a device 2, as previously described.

The method, in particular the cell exposure of epithelial cells at the ALI as shown, can be divided into three phases, namely (1) generation of an aerosol cloud, preferably by atomization of a liquid and the "free fall" of the cloud generated, (2) misting and homogenization (even distribution) of the cloud in the exposure chamber by means of vortex formation, and (3) descension of the aerosol mist onto the cells. FIG. 3a thereby corresponds to phase (1), FIG. 3b to phase (2) and FIG. 3c to phase (3).

According to phase 1, first a, for example, pharmaceutical or toxic substance is fed into the aerosolizing device 1, for example by pipetting (typically about 200 µl). The aerosolizing device is activated and generates an aerosol cloud, preferably a cloud of droplets. The cloud may have an initial velocity and is particularly so dense that the laws of cloud movement apply, resulting in particular in a rapid "free" fall of the cloud (gravity) and thus a fast convective transport of the substance or active agent to the cells.

In phase 2, having arrived at the base, the cloud is laterally distracted uniformly in all directions A, wherein symmetric vortices W are formed which lead [sic] to a horizontally uniform distribution of the cloud and thus the formation of a (droplet) mist N in the lower portion of the chamber. Upon further nebulization activity, the mist fills the chamber gradually from bottom to top, wherein due to gravity, the mist is always most dense near the base.

Finally, after completion of nebulization in the third phase, due to gravity, the mist descends to the sample(s) lying on the base as indicated by the arrows S in FIG. 3c, in approx. 3 min and less. The cell(s) preferably exist in a standard microtiter plate as cultured ALI cells and as a result of the descension of the mist, are uniformly wetted. During the formation of such mist N, the particle concentration near the base region 6 or close to the positioning device 8 is generally higher than it is further away from the base region. This is indicated by the darkening shading in FIG. 3c.

A particularly rapid, highly efficient and horizontally uniform coating of cells at the air-liquid interface (ALI) can thus be achieved. Handling of the device requires no expert knowledge of aerosol or cloud physics; it is easy to use and clean, and is not prone to error or failure.

Furthermore, it is self-evident that other elements such as the ones mentioned above, particularly in connection with FIGS. 1 and 2, can be used in the process described as follows. The method is furthermore preferably carried out with the described device 2.

Generally, the size and density of the cloud as well as the exact dimensions of the vertical side walls 4a, 4b, 4c and 4d and of the base region 6 or the positioning device 8, and the distance D of the aerosolizing device 14 from the positioning device 8 and the vertical extent L of the side walls 4a, 4b, 4c and 4d parameters, help to ensure or improve a rapid and uniform wetting of the sample with the substance.

In particular, the device and method according to the invention allow for a simple and reliable generation of a thin, uniform liquid film, preferably about 15-100 µm, on flat (and structured) surfaces. Thus, it is potentially not only applicable for ALI cell cultures but generally also for the production of micrometer-thin uniform layers on horizontal surfaces.

What is advantageous here, in particular, is the inherently active or intrinsic homogenization of the wetting, which for example, can do without additional measures such as generating an electric field or an additional air flow or mixing system. The method in particular achieves a uniform distribution of the aerosol particles on the cells. This is achieved in particular through the use of cloud physical effects that are favored by an optimal design in terms of the following parameters: (1) geometric dimension of the exposure chamber, (2) positioning of the nebulizer [sic](3) substance or liquid release by the nebulizer per time unit (output rate) and (4) a suitable diameter and initial velocity of the aerosol cloud generated by the nebulizer.

Results of Exemplary Tests

Experiments carried out with the device 2, in particular the one described above, resulted in the following parameters:

When using the device 2, a high deposition factor of more than 0.8, or more than 80%, is achieved. In other words, more than 80% of a liquid or aerosol used is deposited onto the base plate (if necessary, with the positioning device 8). This was determined by atomizing a fluorescein solution as a surrogate for an active pharmaceutical ingredient. This was concluded from data of at least 6 samples with an area of approx. 4.5 $cm^2$ each which were distributed to at least 6 different locations on the base plate and converted to the total area of the base plate (125 $cm^2$).

Further, the total dose applied is very reproducible. With repeated nebulization of 200 µl of fluorescein solution, a maximum deviation [sic] of approximately +/−10% (95% confidence level) was measured of the total dose deposited on average on the 6 samples.

Furthermore, a uniform distribution of the active ingredient on the different wells (6-well Transwell insert) of a microtiter plate was measured. The deviation of the dose in the individual wells from the average dose in all wells was in particular less than +/−20% (95% confidence level).

Furthermore, active substance deposition rates of up to 0.5 µl/$cm^2$/min were measured. This is the volume of the active agent (substance) per cell-covered area per time. Furthermore, when using the device and method according to the invention, no negative effects on biological samples due to handling during exposure could be determined. In particular, cells of a human pulmonary cell line (A549) to which a (non-toxic) physiological saline solution was applied during use of the inventive device show no reduction in viability (WST-1) nor an onset of necrosis (LDH). This is an advantage when using the method with biological samples.

In addition, it was demonstrated that A549 cells in device 2 are not only viable, but may also be used for the systematic study of efficacy of new substances (drug screening). If a non-polarized lung cell line (here: A549), i.e. cells that do not organize themselves differently on the liquid side in comparison with the air side, is used, it must be expected that the biological response of cells at the ALI (in device 2) is the same as under submerged culture conditions for which the active ingredient is pipetted into the media. On the other hand, if polarized lung epithelial cells (e.g. primary cells) are used, significant differences in the biological response can be expected. After stimulation of A549 cells with the tumor necrosis factor α (TNF α), the interleukin 8 (IL-8) as inflammatory marker is induced approximately 7-fold (corresponds to value 1 in FIG. 4), relative to the basal value (non-stimulated cells). The inflammatory effect can be dose-dependently reduced by up to a factor of 2 by applying an anti-inflammatory agent (here, Bortezomib, a proteasome inhibitor). It becomes apparent that after administration of the substance in aerosolized form with device 2, the dose-response curve is identical to the reference curve which was generated by pipetting the substance directly on the cells. This exemplifies that with device 2, aerosolized active substances can be applied accurately dosed and without loss of bioactivity (e.g. due to shear stresses during nebulization) on human pulmonary cells at the ALI. Thus, device 2 is suitable for the systematic screening of substances with respect to their potential as an active ingredient in aerosolized form.

FIG. 4 shows the dose-dependent anti-inflammatory effect of the proteasome inhibitor Bortezomib on a human, non-polarized, pulmonary cell line (A549) at the ALI that was stimulated with inflammatory tumor necrosis factor α (TNFα). Here, the dose-response curve (red, ALI) created with the device 2 does not differ from the reference curve (blue, SUB) which was measured by pipetting the substance on the submerged, cultured cells. This device 2 is thereby validated as a tool for quantitative drug screening for aerosolized liquid substances.

The invention also includes the precise or exact expressions, characteristics, numerical values or ranges, etc., of the expressions, characteristics, numerical values or ranges that are or were associated, above or below, with expressions such as "approximately, about, around, essentially, in general, at least, at a minimum", etc. (i.e. "about 3" shall also include "3", or "essentially radially" shall include "radially", and vice versa). Furthermore, the term "or" can also be "and/or".

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for wetting at least one sample by an aerosol, the device comprising:
   side walls;
   a base region bounded by the side walls; the base region being adapted for receiving or for interacting with a positioning device that positions the at least one sample;
   a cover region that is vertically opposite the base region and delimited by the side walls; and
   an aerosolizing device generating an aerosol is arranged in a vicinity of the cover region, the aerosolizing device being arranged above the base region such that the aerosolizing device at least partially covers the base region in a vertical plan view,
   wherein the device forms an exposure chamber,
   wherein the device is configured to operate without external air flow into or out of the device, and
   wherein the aerosolizing device is arranged approximately 5 cm to 50 cm above the base region or the positioning device.

2. The device according to claim 1, wherein the aerosolizing device has at least one nebulizer.

3. The device according to claim 1, wherein the device and/or the aerosolizing device are designed to form an aerosol cloud.

4. The device according to claim 1, wherein the device is configured to be airflow-free and to operate the nebulizer airflow-free.

5. The device according to claim 1, wherein the aerosolizing device is oriented so that the initial direction of movement of the cloud forms an angle smaller than 30° with the vertical and is essentially parallel to a vertical.

6. The device according to claim 1, wherein in the vertical plan view, the aerosolizing device is arranged approximately centrically above the base region or the positioning device.

7. The device according to claim 1, wherein the device is configured such that a cloud initially generated by the aerosolizing device is such, that an average rate of fall of the cloud generated at the beginning of the exposure is greater than 1 cm/s, greater than 3 cm/s, or greater than 10 cm/s.

8. The device according to claim 1, wherein the device is configured such that an aerosol cloud generated by the aerosolizing device is such that the aerosol cloud descends unobstructed and thus guarantees a rapid transport of the aerosol to the base region.

9. The device according to claim 1, wherein the exposure chamber is dimensioned such that a horizontal cross-sectional area of the exposure chamber in the upper half of the chamber is more than 2-fold, 2.5-fold, or more than 3-fold as large as a cross-sectional area of an aerosol cloud initially generated.

10. The device according to claim 1, further comprising a positioning device for positioning the at least one sample along the base region.

11. The device according to claim 1, wherein the device and/or the positioning device is/are formed to receive or to wet a sample.

12. The device according to claim 1, wherein the sample has biological material and/or material samples.

13. The device according to claim 1, wherein the positioning device comprises elements for measuring and/or regulating temperature, elements for supplying the sample, or elements for measuring the weight of the substance deposited on one or more samples.

14. A method for wetting at least one sample by an aerosol with the device according to claim 1, the method comprising:
   providing the at least one sample in the exposure chamber;
   generating an aerosol cloud above the at least one sample at a position that at least partially covers the base region in the vertical plan view; and
   allowing the aerosol cloud to descend in a direction of the sample.

15. The method according to claim 14, wherein as the aerosol cloud descends in the direction of the at least one sample, the aerosol cloud forms vortices that transform the cloud into a mist that uniformly fills the exposure chamber in a horizontal direction.

16. The method according to claim 15, wherein the mist descends gravitationally in the direction of the sample.

17. The method according to claim 14, further comprising the step of formation of vortices in the aerosol cloud by impingement of the aerosol cloud on the base region and/or the positioning device that provides the sample.

18. The method according to claim 14, further comprising the step of forming a mist, wherein the mist descends gravitationally onto the at least one sample.

19. The method according to claim 14, further comprising the step of providing an airflow-free aerosolizing device and/or an airflow-free nebulizer as the aerosolizing device to generate the aerosol.

20. The method according to claim 14, further comprising a spatial uniform wetting of the at least one sample.

21. The device according to claim 13, wherein the element for measuring and/or regulating temperature is a heater or an electrical temperature control device operated by a water circuit,
   wherein the element for supplying the sample is a culture medium, and
   wherein the elements for measuring the weight of the substance deposited on one or more samples are one or more quartz crystal microbalances.

22. The device according to claim 1, wherein the aerosolizing device is arranged approximately 7 cm to 50 cm above the base region or the positioning device.

23. The device according to claim 1, wherein the aerosolizing device is arranged approximately 9 cm to 20 cm above the base region or the positioning device.

* * * * *